(12) United States Patent
Mori et al.

(10) Patent No.: US 10,561,540 B2
(45) Date of Patent: Feb. 18, 2020

(54) PRODUCTION METHOD FOR UNDER PANTS-TYPE DISPOSABLE DIAPER AND UNDER PANTS-TYPE DISPOSABLE DIAPER CAPABLE OF BEING PRODUCED BY SAID PRODUCTION METHOD

(71) Applicant: DAIO PAPER CORPORATION, Ehime (JP)

(72) Inventors: Yosuke Mori, Ehime (JP); Sadanao Manabe, Tokyo (JP)

(73) Assignee: DAIO PAPER CORPORATION, Ehime (JP)

( * ) Notice: Subject to any disclaimer, the term of this patent is extended or adjusted under 35 U.S.C. 154(b) by 444 days.

(21) Appl. No.: 15/120,395

(22) PCT Filed: Feb. 26, 2015

(86) PCT No.: PCT/JP2015/055559
§ 371 (c)(1),
(2) Date: Aug. 19, 2016

(87) PCT Pub. No.: WO2015/137129
PCT Pub. Date: Sep. 17, 2015

(65) Prior Publication Data
US 2017/0065463 A1   Mar. 9, 2017

(30) Foreign Application Priority Data
Mar. 13, 2014  (JP) ................................ 2014-049884
Dec. 15, 2014  (JP) ................................ 2014-253117

(51) Int. Cl.
*A61F 13/15*   (2006.01)
*A61F 13/496*  (2006.01)
*A61F 13/49*   (2006.01)

(52) U.S. Cl.
CPC .. *A61F 13/15804* (2013.01); *A61F 13/15593* (2013.01); *A61F 13/15723* (2013.01);
(Continued)

(58) Field of Classification Search
CPC .......... A61F 13/15593; A61F 13/15804; A61F 13/49011; Y10T 156/1015; Y10T 156/1051; B32B 2555/02
See application file for complete search history.

(56) References Cited

U.S. PATENT DOCUMENTS

2010/0252178 A1   10/2010   Takino et al.
2011/0288517 A1*  11/2011   Mori ................. A61F 13/15756
                                                  604/385.3
(Continued)

FOREIGN PATENT DOCUMENTS

EP   2186493 A1   5/2010
EP   2387982 A1   11/2011
(Continued)

*Primary Examiner* — Carson Gross
(74) *Attorney, Agent, or Firm* — Muncy, Geissler, Olds & Lowe, P.C.

(57) ABSTRACT

The present invention provides a production method for an underpants-type disposable diaper in space-saving and simple facilities while reducing the risk of occurrence of wrinkles, including: supplying a continuous sheet material in the continuous direction thereof; disposing resilient and elastic members for imparting elasticity to a ventral side outer body and a dorsal side outer body at a CD direction intermediate portion of the sheet material; folding CD direction one side and other side parts across the CD direction intermediate portion toward the side of the CD direction intermediate portion with the resilient and elastic members, sandwiching and fixing the resilient and elastic members in the folded sheet material, and joining together the folded parts and the CD direction intermediate portion to form a continuous elastic belt; cutting the elastic belt at a CD (Continued)

direction intermediate position to obtain a dorsal side elastic belt and a ventral side elastic belt, and then assembling an inner body to the dorsal side elastic belt and the ventral side elastic belt.

6 Claims, 12 Drawing Sheets

(52) U.S. Cl.
CPC .. *A61F 13/15747* (2013.01); *A61F 13/15764* (2013.01); *A61F 13/496* (2013.01); *A61F 13/49011* (2013.01); *B32B 2555/02* (2013.01); *Y10T 156/1015* (2015.01); *Y10T 156/1051* (2015.01)

(56) References Cited

U.S. PATENT DOCUMENTS

| | | | |
|---|---|---|---|
| 2013/0110073 A1 | 5/2013 | Umebayashi | |
| 2013/0255862 A1* | 10/2013 | Schneider | A61F 13/15593 156/161 |
| 2014/0000794 A1* | 1/2014 | Hamilton | A61F 13/49011 156/163 |

FOREIGN PATENT DOCUMENTS

| | | | | |
|---|---|---|---|---|
| JP | 2009-061045 A | | 3/2009 | |
| JP | 2009-160129 A | | 7/2009 | |
| JP | 2011-212373 A | | 10/2011 | |
| JP | 2011212373 A | * | 10/2011 | ....... A61F 13/15593 |
| JP | 2014-004115 A | | 1/2014 | |
| WO | WO 2013/148379 A1 | | 10/2013 | |

* cited by examiner

PRODUCTION METHOD FOR UNDER PANTS-TYPE DISPOSABLE DIAPER AND UNDER PANTS-TYPE DISPOSABLE DIAPER CAPABLE OF BEING PRODUCED BY SAID PRODUCTION METHOD

TECHNICAL FIELD

The present invention relates to a production method for an underpants-type disposable diaper and an underpants-type disposable diaper capable of being produced by the production method.

BACKGROUND ART

As a form of an underpants-type disposable diaper, there is known an underpants-type disposable diaper including: a cylindrical outer body that is formed by joining a ventral side outer body and a dorsal side outer body at both sides; and an inner body that has a front part joined to a width direction central area of the ventral side outer body and a back part joined to a width direction central area of the dorsal side outer body and passes through the crotch portion of a wearer, the ventral side outer body and the dorsal side outer body being separated without being continued (for example, refer to Patent Document 1). In such an outer halved type, the ventral side outer body and the dorsal side outer body are not continued but separated at the crotch side, which provides an advantage that there is no need to punch leg openings for passage of the wearer's legs, or if there is a need, only small-area leg openings is enough. That is, as cut pieces (hereinafter, also called trims) are discarded, the material loss (hereinafter, also called trim loss) can be suppressed.

As a method for manufacturing the outer halved-type diapers, in general, the ventral side outer body and the dorsal side outer body are separately fabricated from belt-like continuous sheet materials, and the form illustrated in FIG. 1 of Patent Document 1 is also categorized as this method. In this case, it is necessary to provide an assembly line for the ventral side outer body and an assembly line for the dorsal side outer body in parallel to convey the outer bodies in parallel, which makes the production facilities larger and more complicated. This problem can be solved by supplying one belt-like continuous sheet material in a MD direction (mechanical direction or conveyance direction. The lateral direction orthogonal to this direction is called a CD direction) and disposing resilient and elastic members on the sheet material, and folding back the sheet material to cover the resilient and elastic members, then cutting the sheet material continuously in the direction parallel to the MD direction to divide the sheet material into a ventral side elastic belt and a dorsal side elastic belt, and then conveying the belts separated from each other in parallel in a width direction as described in paragraph 0037, Patent Document 1. In this case, however, at the step of folding back the sheet material, the wide sheet material is folded into two. This is not only making the folding facility (sailor) larger but causing a problem that it is difficult to fold the sheet material neatly without wrinkles. In addition, the edge of the waist of either the ventral side outer body or the dorsal side outer body may not make a fold in the sheet material (excellent in texture without turn-up of the sheet material) but may deteriorate in texture and appearance. Additionally, as described in Patent Document 1, when the wide sheet material is folded into two, the edges of the sheet material are likely to be misaligned, and the misalignment remains at the edge of the waist of the diaper to contribute to deterioration in texture and appearance.

CITATION LIST

Patent Document

Patent Document 1: JP-A No. 2009-061045
Patent Document 2: JP-A No. 2009-160129

SUMMARY OF INVENTION

Problems to be Solved by the Invention

A major object of the present invention is to allow production at space-saving and simple facilities, while reducing the risk of occurrence of wrinkles or the like.

Means for Solving the Problem

The present invention for solving the foregoing problems is as follows:

A production method for an underpants-type disposable diaper including: an outer body that is formed by joining a ventral side outer body and a dorsal side outer body at both sides; and an inner body that has a front part joined to a width direction central area of the ventral side outer body and a back part joined to a width direction central area of the dorsal side outer body and passes through the crotch portion of a wearer, the ventral side outer body and the dorsal side outer body being separated without being continued at the crotch side, wherein the production method comprises: supplying a belt-like continuous sheet material in the direction of continuity; disposing resilient and elastic members for imparting elasticity to the ventral side outer body and the dorsal side outer body at a CD direction intermediate portion of the sheet material; folding CD direction one side and other side parts across the CD direction intermediate portion of the sheet material toward the side of the CD direction intermediate portion with the resilient and elastic members, sandwiching and fixing the resilient and elastic members between the folded parts and the CD direction intermediate portion, and joining together the folded parts and the CD direction intermediate portion to form a belt-like continuous elastic belt; cutting the elastic belt at a CD direction intermediate position to split the elastic belt into a dorsal side elastic belt and a ventral side elastic belt, and then increasing a CD direction space between the dorsal side elastic belt and the ventral side elastic belt; supplying the separately produced inner body at MD direction intervals, joining the front part of the inner body to the ventral side elastic belt and the back part of the inner body to the dorsal side elastic belt to form an inner assembly body; and folding double the inner assembly body in the CD direction, joining the ventral side elastic belt and the dorsal side elastic belt at parts to be both sides of each individual diaper, and cutting off the ventral side elastic belt and the dorsal side elastic belt at boundaries of each individual diaper to produce each individual diaper.

(Operation and Effect)

The present invention is the same as the method described in Patent Document 1 in that the elastic belt assembled by folding one sheet material is divided to form the ventral side elastic belt and the dorsal side elastic belt. However, the sheet material is folded such that the CD direction one side and other side parts across the CD direction intermediate portion of the sheet material are folded toward the side of the CD direction intermediate portion with the resilient and elastic members (so-called C-folding) respectively. Accordingly, the folding width of the sheet material is significantly smaller, the folding facility (sailor) can be made compact, and the material sheet can be easily folded in a neat and wrinkle-free manner. In addition, the both waist edges of the ventral side outer body and the dorsal side outer body constitute folds in the sheet material to make the diaper excellent in texture and appearance at the waist edge.

The production method for an underpants-type disposable diaper, wherein, at the time of cutting the elastic belt, the elastic belt is cut at a position passing through a position of joining between the folded parts and the CD direction intermediate portion.
(Operation and Effect)

By cutting the elastic belt at the position passing through the position of the folding and joining in the sheet material, leg-side edges of the ventral side outer body and the dorsal side outer body are formed without misalignment in the sheet material and are unlikely to be turned up, thereby providing favorable texture.

The production method for an underpants-type disposable diaper, wherein, at the time of formation of the elastic belt, the CD direction one side part and other side part of the sheet material are folded to form an overlapped portion between an end of the folded part on the CD direction one side and an end of the folded part on the CD direction other side.
(Operation and Effect)

By overlapping the ends of the folded parts, it is possible to improve the appearance due to a decreased number of level differences at the ends, and to avoid reduction in the strength caused by the formation of a part of the outer body from the single-layer sheet material.

The production method for an underpants-type disposable diaper, wherein the resilient and elastic members and a fixing means therefor, and a joining means for the sheet material are not provided in a region corresponding to the partial or entire overlapped portion in the sheet material, and the sheet material in the region is joined only by the joining between the ventral side elastic belt and the dorsal side elastic belt.

The overlapped portion of the folded parts is thick and high in stiffness. Accordingly, when the resilient and elastic members and the fixing means therefor (adhesive or the like) exist on the overlapped portion, the overlapped portion becomes lower in air permeability and flexibility. Therefore, it is also preferred that the resilient and elastic members and the fixing means therefor, and the joining means for the sheet material are not provided in a region corresponding to the partial or entire overlapped portion in the sheet material to improve air permeability and flexibility as described above. In the thus formed region, each layer of the outer body is joined together by the joining of the ventral side elastic belt and the dorsal side elastic belt, and therefore the strength of the entire diaper is not largely lowered.

The production method for an underpants-type disposable diaper, wherein, at the time of formation of the elastic belt, the CD direction one side and other side parts of the sheet material are folded such that the folded part on the CD direction one side and the folded part on the CD direction other side are separated from each other in the CD direction.
(Operation and Effect)

Accordingly, at least part of at least one of the ventral side outer body and the dorsal side outer body is formed from the single-layer sheet material at the separation portion between the folded parts. This separation portion can improve air permeability and flexibility.

The production method for an underpants-type disposable diaper, wherein the folded parts are positioned inside the diaper.
(Operation and Effect)

When the folded parts are overlapped at the ends, butted against each other, or separated from each other, steps, seams, or flaps are formed at the folded parts. However, by being positioned inside the diaper, the folded parts are less prominent in outer appearance.

The production method for an underpants-type disposable diaper, wherein the folded parts are positioned outside the diaper.
(Operation and Effect)

When the folded parts are overlapped at the ends, butted against each other, or separated from each other, steps, seams, or flaps are formed at the folded parts. However, by being positioned outside the diaper, the folded parts can be used to improve the appearance as accents on the outer appearance. For example, flaps may be positively used to form frills and pockets.

The production method for an underpants-type disposable diaper, wherein, after the formation of the elastic belt, some of the resilient and elastic members in a region to be the ventral side elastic belt and some of the resilient and elastic members in a region to be the dorsal side elastic belt are finely divided before the elastic belt is split into the ventral side elastic belt and the dorsal side elastic belt.
(Operation and Effect)

In a general production method for an underpants-type disposable diaper, before the inner body is assembled, the resilient and elastic members overlapping the inner body are finely divided by a method such as cutting or heat embossing. The division region of the resilient and elastic members is positioned at the width direction center of the diaper, and the right and left sides of the division region constitute elastic ranges. However, when the resilient and elastic members are divided after the elastic belt is split into the dorsal side elastic belt and the ventral side elastic belt, the MD direction positions of the division regions in the dorsal side elastic belt and the ventral side elastic belt may be slightly misaligned with each other. This misalignment causes another misalignment between the right and left elastic ranges. This may easily deteriorate visual quality and disturb attachment balance. In contrast to this, by dividing the resilient and elastic members before the splitting of the elastic belt into the dorsal side elastic belt and the ventral side elastic belt, the MD direction position of the division region is aligned between the dorsal side elastic belt and the ventral side elastic belt. In addition, this method also provides an advantage of making the facility for rubber thread division compact.

The production method for an underpants-type disposable diaper, wherein at least the CD direction central end portion of at least one of the dorsal side elastic belt and the ventral side elastic belt is formed as a region in which a plurality of layers in the sheet material is layered by forming the elastic belt and splitting the elastic belt into the dorsal side elastic belt and the ventral side elastic belt, and cutting is performed within the region to form edges of leg openings in a curved shape.
(Operation and Effect)

As described above, when the sheet material has two or three layers in the entire cut portion for forming the edges of the leg openings in a curved shape and does not include the single-layer separation portion, the number of layers in the sheet material is large in the site including the cut position and the sheet material is joined together at the resilient member attachment step. Accordingly, the portion to be cut are higher in stiffness, easier to cut (a misalignment is unlikely to occur at the time of cutting), and higher in operational stability.

An underpants-type disposable diaper, including: an outer body that is formed by joining a ventral side outer body and a dorsal side outer body at both sides; and an inner body that has a front part joined to a width direction central area of the ventral side outer body and a back part joined to a width direction central area of the dorsal side outer body and passes through the crotch portion of a wearer, the ventral side outer body and the dorsal side outer body being separated without being continued at the crotch side, wherein the ventral side outer body and the dorsal side outer body have an inner layer and an outer layer formed by folding the sheet material on the waist side, and resilient and elastic members are provided between the inner layer and the outer layer, and in the ventral side outer body and the dorsal side outer body, both the inner layer and the outer layer extend up to edges of the crotch side, one of the ventral side outer body and the dorsal side outer body has an edge sheet material intervening between a leg-side edge portion of the outer layer and the inner layer, the edge sheet material and the inner layer are joined together, and the edge sheet material and the outer layer are not joined together at parts other than the both lateral sides of the outer body.

(Operation and Effect)

According to this configuration, the leg-side edge portions of the outer layer protrude and exhibit frill-like appearance, thereby making the diapers suitable in particular for paper diapers for girls. In addition, the leg-side edges of the ventral side outer body and the dorsal side outer body are formed without misalignment in the sheet material and are unlikely to be turned up, thereby providing favorable texture. In addition, the edge sheet material and the outer layer are not joined together at parts other than the both side parts of the outer body, thereby providing favorable air permeability in the regions with the edge sheet material.

An underpants-type disposable diaper, including: an outer body that is formed by joining a ventral side outer body and a dorsal side outer body at both sides; and an inner body that has a front part joined to a width direction central area of the ventral side outer body and a back part joined to a width direction central area of the dorsal side outer body and passes through the crotch portion of a wearer, the ventral side outer body and the dorsal side outer body being separated without being continued at the crotch side, wherein the ventral side outer body and the dorsal side outer body have an inner layer and an outer layer formed by folding the sheet material on the waist side, and resilient and elastic members are provided between the inner layer and the outer layer, and in the ventral side outer body and the dorsal side outer body, both the inner layer and the outer layer extend up to edges of the crotch side, one of the ventral side outer body and the dorsal side outer body has an edge sheet material provided on an outer surface of leg-side edge portion of the outer layer, the edge sheet material is joined to the outer body at only the crotch-side edge portion and the both lateral side parts of the outer body, and at least the leg-side edge is formed from the inner layer and the outer layer.

(Operation and Effect)

According to this configuration, the portion between the edge sheet material and the outer layer is formed as a pocket-like portion opened on the waist side. In addition, the leg-side edges of the ventral side outer body and the dorsal side outer body are formed without a misalignment in the sheet material, and are unlikely to be turned up, thereby providing favorable texture. Further, most of the overlapped portion of the edge sheet material and the outer layer are not joined together, thereby providing favorable air permeability in the region with the edge sheet material.

Advantageous Effects of Invention

As described above, according to the present invention, it is possible to provide advantages such as enabling production in space-saving and simple facilities, while reducing the risk of occurrence of wrinkles.

DESCRIPTION OF EMBODIMENTS

An embodiment of the present invention will be described below in detail with reference to the accompanying drawings.

<Example of Production Method for an Underpants-Type Disposable Diaper>

Figure 1:
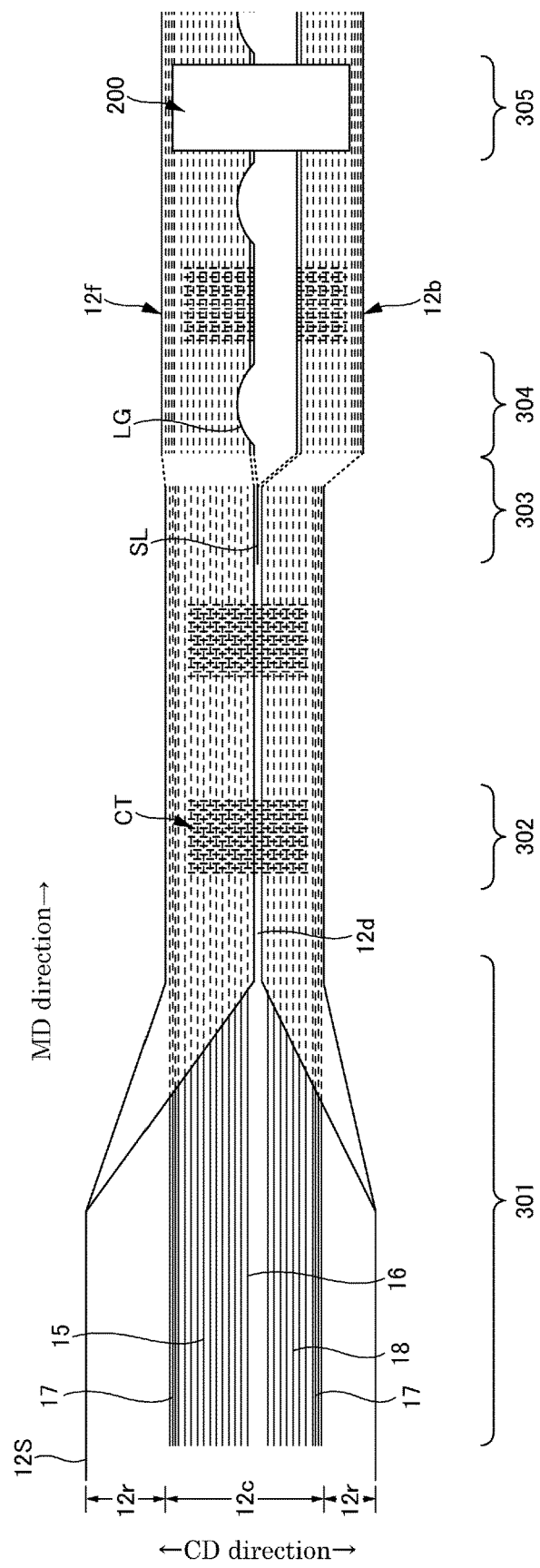
FIG. 1 is a schematic plane diagram describing a production flow.
Figure 2:
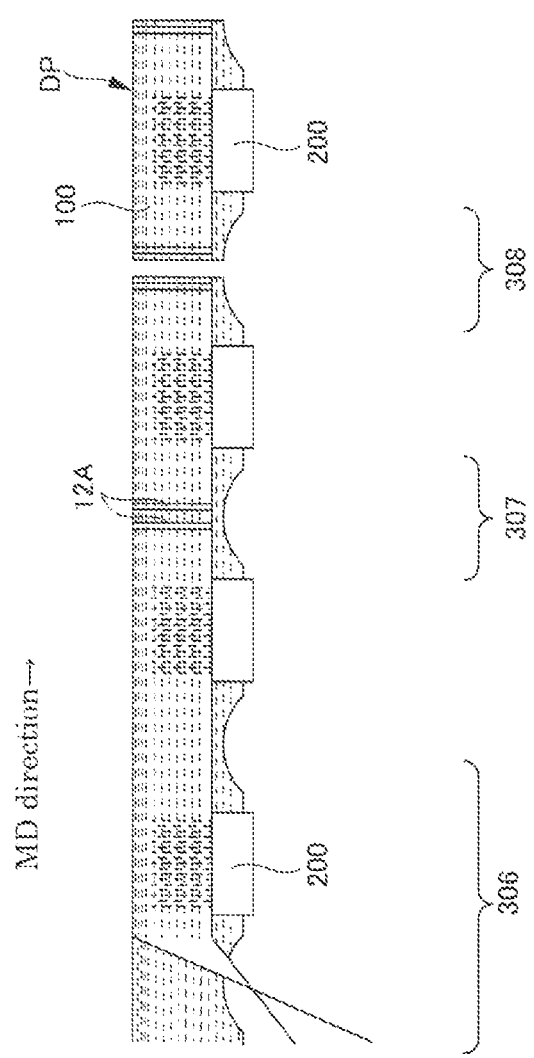
FIG. 2 is a schematic plane diagram describing the production flow.

FIGS. 1 and 2 illustrate an example of a production method for an underpants-type disposable diaper. The production line is formed for a lateral flow with the diaper width direction in parallel to the MD direction (machine direction or line flow direction). In the production line, a ventral side elastic belt 12f to be a ventral side outer body 12F and a dorsal side elastic belt 12b to be a dorsal side outer body 12B are formed, and an inner body 200 produced in another line is attached to the ventral side elastic belt 12f and the dorsal side elastic belt 12b. For the sake of ease of understanding, the continuous members in the production process are given the same reference signs as those of the members after the production.

More specifically, the production line has a resilient member attachment step 301, a resilient member cutting step 302, a center slit step 303, a leg opening cutting and splitting step 304, an inner body attachment step 305, a folding step 306, a side part joining step 307, and a cutoff step 308.

Among these steps, the resilient member attachment step 301 is mainly more characteristic than the conventional production method.

Specifically, at the resilient member attachment step 301, while a belt-like continuous sheet material 12S with a specific width is conveyed in the direction of continuity, a large number of resilient and elastic members 15 to 18 are supplied in the MD direction extended state with the CD direction space therebetween in a CD direction intermediate portion 12c of a sheet material 12S to impart elasticity to the ventral side outer body 12F and the dorsal side outer body 12B, parts 12r of the sheet material 12S on CD direction one side and other side across the CD direction intermediate portion 12c are folded to the side of the CD direction intermediate portion 12c with the resilient and elastic members 15 to 18, the resilient and elastic members 15 to 18 are sandwiched and fixed between the folded parts 12r and the CD direction intermediate portion 12c, and the folded parts 12r and the CD direction intermediate portion 12c are joined together to form the belt-like continuous elastic belt.

At the resilient member attachment step 301, the sheet material 12S is folded such that the CD direction one side and other side parts 12r across the CD direction intermediate portion 12c of the sheet material 12S are folded to the side of the CD direction intermediate portion 12c with the resilient and elastic members 15 to 18 (so-called C-folding). Accordingly, the folding width of the sheet material 12S is significantly smaller, the folding facility (sailor) can be made compact and the material sheet can be easily folded in a neat and wrinkle-free manner. In addition, as seen from the product state described later, the both waist edges of the ventral side outer body 12F and the dorsal side outer body 12B constitute folds in the sheet material 12S to make the diaper excellent in texture and appearance at the waist edge.

The sheet material 12S may be folded in such a manner that the folded part 12r on the CD direction one side and the folded part 12r on the CD direction other side are separated in the CD direction to form a separation portion 12d as illustrated in FIG. 1, or in such a manner that an end of the folded part 12r on the CD direction one side and an end of the folded part 12r on the CD direction other side are overlapped to form a three-layer portion 12k as illustrated in FIGS. 4(d) to 4(f) and 12.

The resilient and elastic members 15 to 18 may be fixed by applying a hot-melt adhesive to outer surfaces of the resilient and elastic members 15 to 18 and adhering with the adhesive to the sheet material 12S, or by applying a hot-melt adhesive to the sheet material 12S and sandwiching the resilient and elastic members 15 to 18 in the sheet material 12S. The resilient and elastic members 15 to 18 may be fixed by the entire longitudinal side to the sheet material 12S or may be fixed only at both width direction ends in each individual diaper.

The folded parts 12r and the CD direction intermediate portion 12c of the sheet material 12S can be joined together by the hot-melt adhesive or a welding means such as heat sealing or ultrasonic welding. There is no particular limitation on the joining pattern, and the folded parts 12r and the CD direction intermediate portion 12c can be continuously joined in both the MD direction and the CD direction. Preferably, the folded parts 12r and the CD direction intermediate portion 12c are intermittently joined in at least either one of the MD direction and the CD direction for improvement in air permeability and flexibility. For example, in the case of joining by a hot-melt adhesive, the parts can be joined in an arbitrary adhesive application pattern using any of various generally-known application methods such as slot coating for surface application without gap, spiral coating and curtain coating for surface application with gaps. In addition, the sheet material 12S may be joined together via the hot-melt adhesive applied to the outer surfaces of the resilient and elastic members 15 to 18 as described above. The fixation of the resilient and elastic members 15 to 18 and the joining of the folded parts of the sheet material 12S may be performed at the same position and with the use of the same fixing means, or may be performed at different positions with the use of the same or different fixing means.

Figure 11:
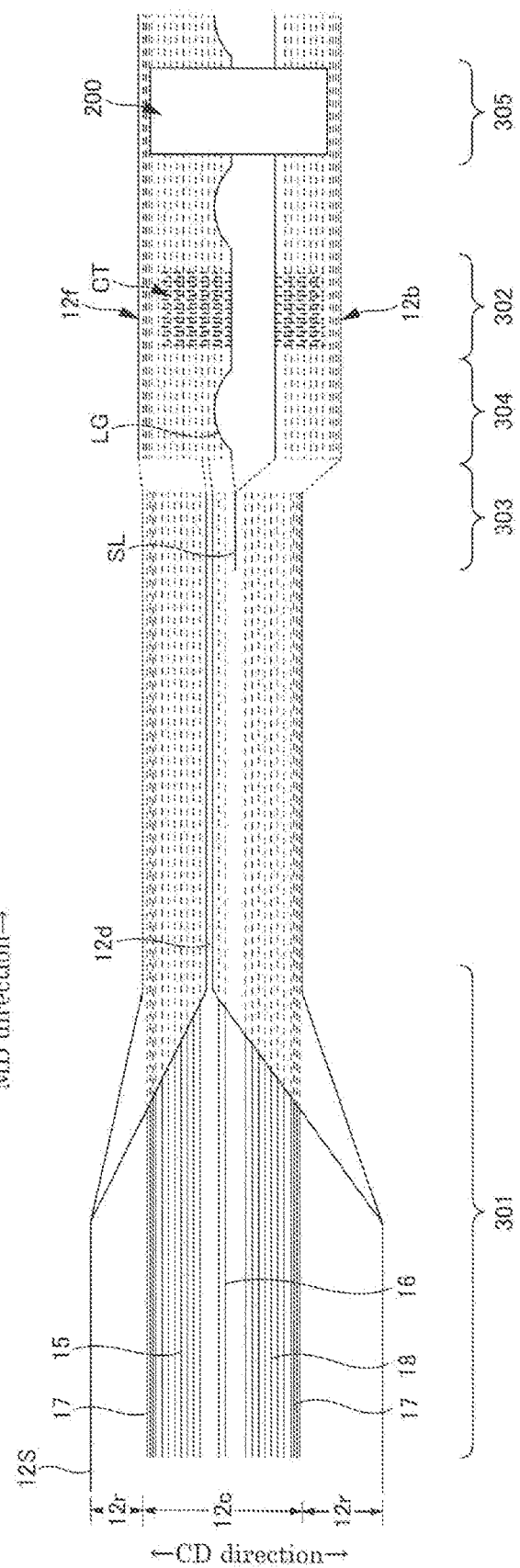
FIG. 11 is a schematic plane diagram describing a production flow.

The thus formed elastic belt is subjected as necessary to the resilient member cutting step 302 prior to the center slit cutting step 303 described later in such a manner that each portion CT of the resilient and elastic members 15 to 18 in a region to be the dorsal side elastic belt 12b and in a region to be the ventral side elastic belt 12f (for example, the partial or entire portion overlapping the inner body 200 described later) is finely divided with MD direction space by a method such as cutting or heat embossing. Accordingly, the stretching force of the resilient and elastic members 15 to 18 does not act on the portions CT. The division can be performed after the center slit cutting step 303 described later as illustrated in FIG. 11. In that case, however, the MD direction positions of the division regions in the dorsal side elastic belt 12b and the ventral side elastic belt 12f will be likely to be misaligned with each other, and the division facility will be increased in size. Accordingly, the division is preferably performed before the center slit cutting step 303. The resilient member cutting step 302 may be omitted.

Figure 3:
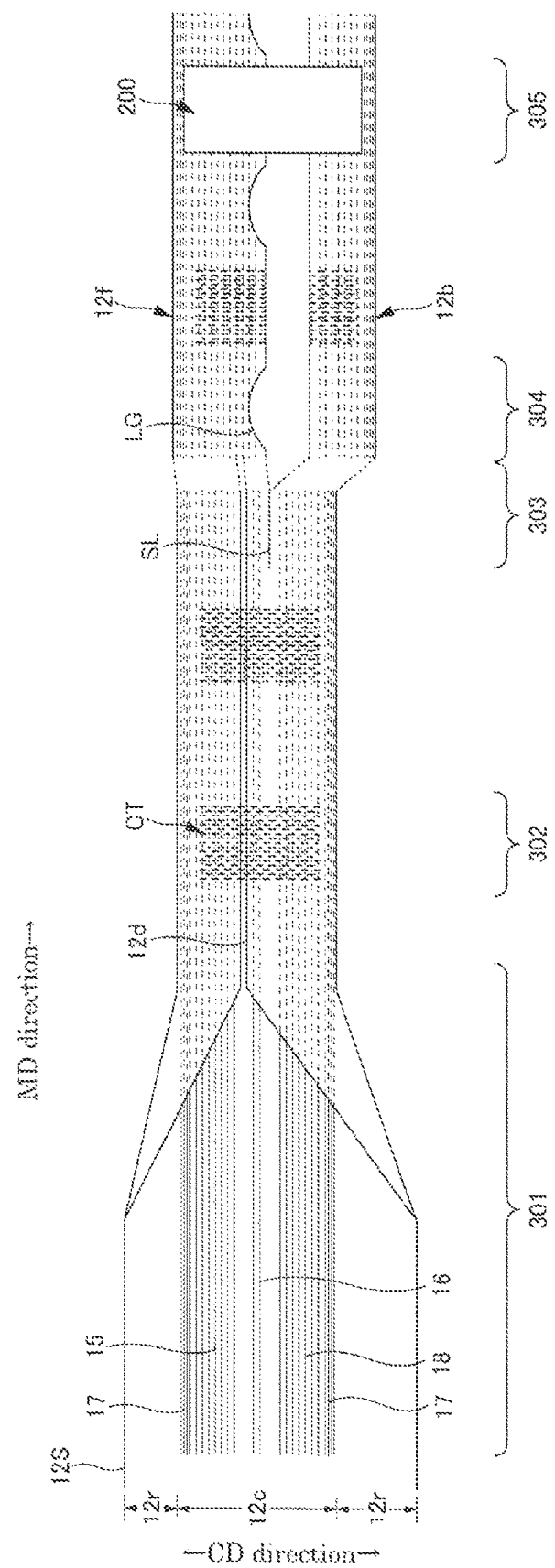
FIG. 3 is a schematic plane diagram describing the production flow.
Figure 12:
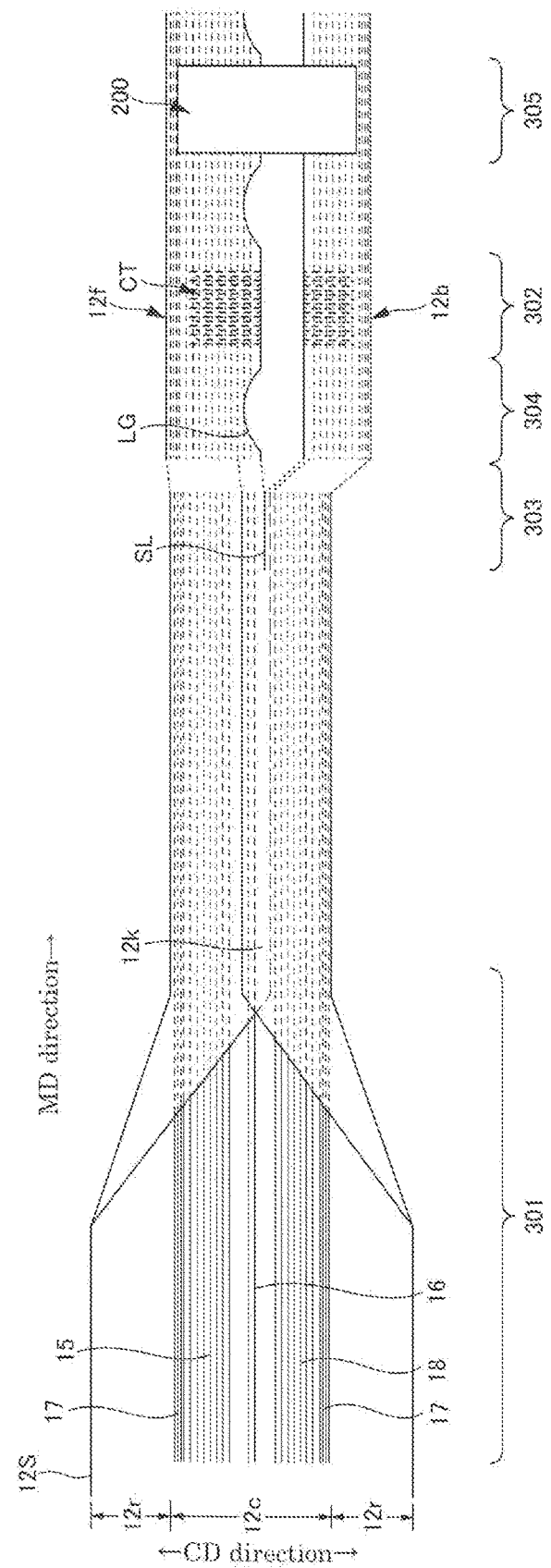
FIG. 12 is a schematic plane diagram describing the production flow.

Then, at the center slit cutting step 303, the elastic belt is cut by a slitter at a predetermined CD direction central site SL to split the elastic belt into the dorsal side elastic belt 12b and the ventral side elastic belt 12f, and CD direction space between the dorsal side elastic belt 12b and the ventral side elastic belt 12f is increased to a predetermined distance. The slit position SL may be at the CD direction center of the elastic belt or may be biased to the ventral side or the dorsal side of the elastic belt. However, as with general pants-type disposable diapers, the slit position SL is preferably biased to the ventral side such that the dorsal side elastic belt 12b is wider than the ventral side elastic belt 12f. In particular, when the slit position SL is at a predetermined CD direction central site in the two-layer portion where the folded part and the non-folded part of the sheet material 12S are overlapped as illustrated in FIGS. 3 and 11, or when the slit position SL is at a predetermined CD direction central site in the three-layer portion 12k formed by overlapping the end of the CD direction one side folded part 12r and the end of the CD direction other side folded part 12r as illustrated in FIG. 12, the number of layers in the sheet material 12S in the site including the slit position SL is large. Accordingly, the portion to be cut is higher in stiffness, easier to cut (misalignment is unlikely to occur at the time of cutting), and higher in operational stability. In addition, when the sheet material 12S is overlapped and joined together by the hot-melt adhesive or the like at the site including the slit position SL and the joining pattern is the pattern which is across the slit position SL (for example, solid, curtain, summit, or spiral pattern), as no misalignment occurs in the sheet material 12S at the time of cutting, the sheet material 12S is even easier to cut and higher in operation stability.

After the center slit cutting step 303, the leg opening cutting and splitting step 304 is performed to cut off a CD direction central side end edge (to be the edges of the leg openings LO) of at least one of the dorsal side elastic belt 12b and the ventral side elastic belt 12f (the dorsal side elastic belt 12b in the illustrated form) at a cutting position LG in a partial or entirely curved shape. At the cut-off portion, the sheet material 12S may include the single-layer separation portion 12d as illustrated in FIG. 1. However, when the CD direction central end portion including the cut-off portion is positioned in a region where the sheet material 12 includes a plurality of layers (does not include the single-layer separation portion) and cutting is performed to form the edges of the leg openings in a curved shape within the region as illustrated in FIGS. 3 and 11, the number of layers in the sheet material 12S at the site including the cutting position LG is large and the sheet material 12S is joined together at the resilient member attachment step 301. Accordingly, the portion to be cut is higher in stiffness, easier to cut (a misalignment is unlikely to occur at the time of cutting), and higher in operational stability. In particular, in the case that the site including the slit position SL is joined in the pattern across the slit position SL, when the cutting blade hits the slit position SL at the first stage of cutting (at an intersection of the slit position SL and the cutting position LG), no misalignment occurs in the sheet material 12S, and the portion to be cut is even easier to cut and higher in operation stability. The leg opening cutting and splitting step 304 can be performed at any timing between the center slit cutting step 303 and the cutoff step 308. To eliminate the trim loss completely, the leg opening cutting and splitting step 304 may be omitted.

After that, at the inner body attachment step 305, the inner body 200 produced in advance in another line is supplied at predetermined intervals in the MD direction. The front part of the inner body 200 is joined to the ventral side elastic belt 12f and the back part of the inner body 200 is joined to the dorsal side elastic belt 12b respectively, thereby to form an inner assembly body. These joining operations can be performed by an appropriate means such as the hot-melt adhesive or heat sealing. In addition, the inner body 200 can be supplied by being formed as a complete body in other line, or by being assembled on the elastic bodies 12f and 12b after being formed as a plurality of parts in the other lines.

Then, at the folding step 306, the inner assembly body is folded at the CD direction center such that an attachment surface of the ventral side elastic belt 12f relative to the inner body 200 and an attachment surface of the dorsal side elastic belt 12b relative to the inner body 200 are overlapped. Then, at the side part joining step 307, the ventral side elastic belt 12f and the dorsal side elastic belt 12b are joined at the both side parts of the individual diaper to form side seal portions 12A. At the cutoff step 308, the ventral side elastic belt 12f and the dorsal side elastic belt 12b are cut off at boundaries of each individual diaper, thereby obtaining each individual diaper DP. The side part joining step 307 and the cutoff step 308 can be performed simultaneously. When the ventral side elastic belt 12f and the dorsal side elastic belt 12b are not identical in width, the side seal portions 12A may be formed only at the overlapped portion of the both elastic belts 12f and 12b, or may be formed at the overlapped portion and the excess portion which is produced on the wider belt.

FIGS. 4(b) to 4(f) illustrate structural examples of the outer bodies 12F and 12B that can be produced by the foregoing production method. FIG. 4(a) shows the form described in paragraph 0037 of Patent Document 1.

Figure 4:
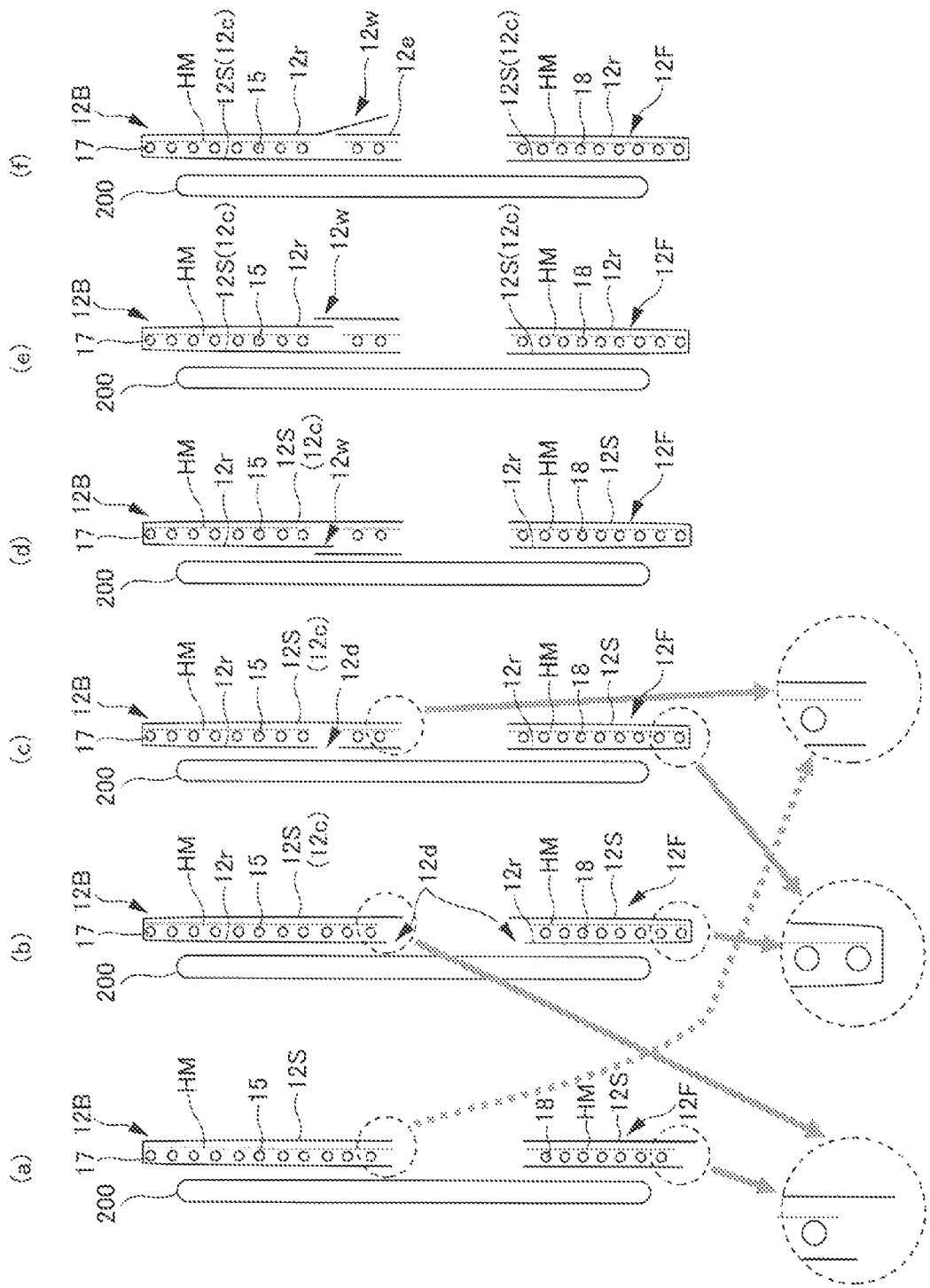
FIGS. 4(a) to (f) are vertical cross-sectional views of major components of an underpants-type disposable diaper.
Figure 5:
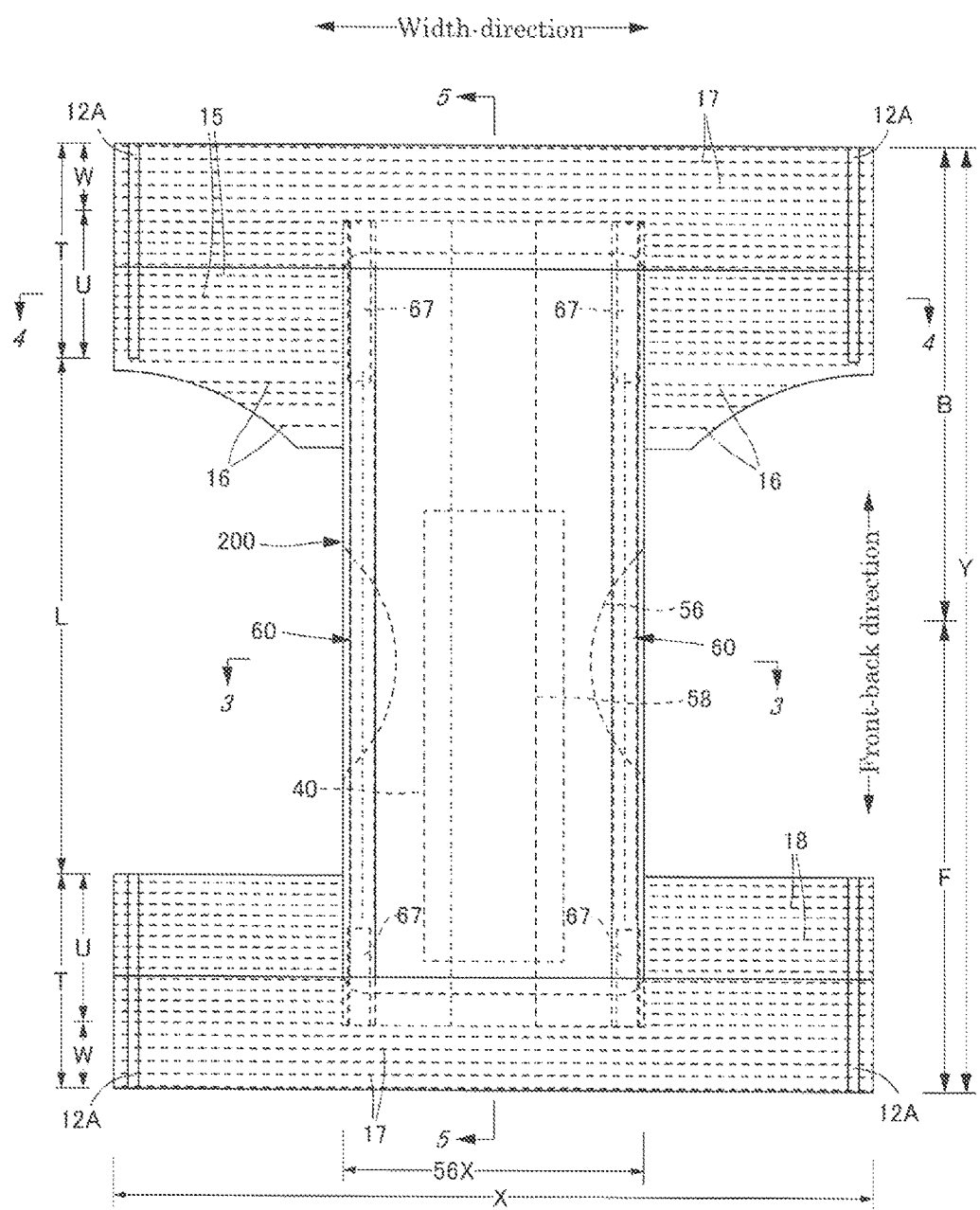
FIG. 5 is a plane view of inside of the pants-type disposable diaper in the open state.

The first form is produced by the method described in FIG. 1. At the formation of the elastic belts, the CD direction one side and other side portions 12r in the sheet material 12S are folded such that the CD direction one side folded part 12r and the CD direction other side folded part 12r are separated from each other in the CD direction. Therefore, as illustrated in FIG. 4(b), at the separation portion 12d between the folded parts 12r, at least part of at least one of the ventral side outer body 12F and the dorsal side outer body 12B is formed from the single-layer sheet material 12S, and the separation portion 12d improves air permeability and flexibility.

In the second form, as illustrated in FIG. 3, the position of the separation portion 12d between the folded parts 12r is biased toward a CD direction one side (the ventral side or the dorsal side of the diaper, and the dorsal side in the illustrated example) relative to the slit position SL at the center slit cutting step 303. In this case, as illustrated in FIG. 4(c), the leg-side edges of both the ventral side outer body 12F and the dorsal side outer body 12B are cut edges of two-layer structure, which provides an advantage that it is unlikely to cause separation between the layers and turn-up of the layers.

The third form is a modification form of the second form. According to the production process illustrated in FIG. 3, at the formation of the elastic belts, the end of the CD direction one side folded part 12r and an end of the CD direction other side folded part 12r are overlapped to form an overlapped portion 12w as illustrated in FIG. 4(d). By overlapping the ends of the folded parts 12r as described above, the number of steps at the ends decreases to improve the appearance. In addition, it is possible to avoid reduction in strength caused by forming part of the outer bodies 12F and 12B from the single-layer sheet material 12S.

In the first to third forms, the folded parts 12r are positioned inside the diaper at the formation of the elastic belts. Accordingly, when the folded parts 12r are overlapped at the ends, butted against each other, or separated from each other, steps, seams, or flaps are formed at the folded parts 12r. However, by being positioned inside the diaper, the folded parts 12r are less prominent in outer appearance. Nevertheless, in the case where the overlapped portion 12w illustrated in FIG. 4(d) is formed, in contrast to the illustrated example, forming the overlapped portion 12w such that the free edge of the overlapped portion 12w is faced to the crotch side would be preferred because the free edge of the overlapped portion 12w does not get caught in the toes of the wearer when the wearer is putting on the diaper.

In the fourth form, in contrast to the first to third forms, the folded parts 12r are positioned outside the diaper at the formation of the elastic belts as illustrated in FIG. 4(e). This makes it possible to use the steps, seams, or flaps formed by the folded parts 12r for improvement of appearance as accents on the appearance. For example, as in the fifth form illustrated in FIG. 4(f), by setting the outer edge of the overlapped portion 12w as a free edge without being joined with the inner edge of the same, the outer edge of the overlapped portion 12w are faced toward the legs and are capable of freely moving like frills. Although not illustrated in detail, the leg side of the overlapped portion 12w in FIG. 4(f) is positioned at the leg-side edge of the dorsal side outer body 12B. Accordingly, when the side seal portions 12A are formed only at the overlapped portion between the both elastic belts, at least part of the leg side of the overlapped portion 12w is not joined to the dorsal side outer body 12B by the side seal portions 12A, and therefore the degree of freedom of the edge of the overlapped portion 12w increases to further improve the appearance. Alternatively, although not illustrated, by providing the overlapped portion 12w in the ventral side outer body 12A (or the dorsal side outer body 12B) and forming the overlapped portion 12w such that the outer edge is faced to the waist side, a pocket-like portion can be formed by the overlapped portion 12w. In this case, the overlapped portion 12w is almost entirely joined by the side seal portions 12A, and therefore the overlapped portion 12w does not lose the function of a pocket.

When the overlapped portion 12w is provided as in the third and fourth forms, the overlapped portion 12w is a thick, high-stiffness portion. Therefore, when the overlapped portion 12w is provided with the resilient and elastic members 15 to 18 and the fixing means therefor (adhesive HM or the like), the overlapped portion 12w deteriorates in air permeability and flexibility. Accordingly, it is also preferred that the region corresponding partially or entirely to the overlapped portion 12w in the sheet material 12S is not provided with the resilient and elastic members 15 to 18 and the fixing means therefor (adhesive HM or the like) or the joining means (adhesive HM or the like) for the sheet material 12S to improve air permeability and flexibility. Only the layer constituting the overlapped portion 12w in the sheet material 12S may not be provided with the resilient and elastic members 15 to 18 and the fixing means therefor (adhesive HM or the like) or the joining means for the sheet material 12S. Preferably in particular, however, all the layers of the outer bodies 12F and 12B forming the overlapped portion 12w are not provided with the resilient and elastic members and the fixing means therefor or the joining member for the sheet material. Even when the overlapped portion is formed in such a manner, the layers in the outer bodies 12F and 12B can be joined to each other at least by the side seal portions 12A. Accordingly, it is possible to improve the overlapped portion 12w in air permeability and flexibility without reducing significantly the strength.

The resilient and elastic members 15 to 18 and the fixing means therefor, and the joining means for the folded parts 12r and the CD direction intermediate portion 12c are related to air permeability and flexibility. Accordingly, the sheet material 12S is preferably joined in an intermittent pattern in at least one of the MD direction and the CD direction. However, in the case of joining the sheet material 12S in an intermittent pattern in the CD direction, when the slit position SL at the center slit cutting step 303 is out of the joining position of the sheet material 12S, the leg-side edges of the ventral side outer body 12F and the dorsal side outer body 12B are likely to be misaligned or turned up in the sheet material 12S, which may lead to deterioration in texture. Accordingly, at the time of cutting the elastic belts, the elastic belts are preferably cut at a position passing through the joining position of the folded parts and the CD direction intermediate portion 12c. Accordingly, the leg-side edges of the ventral side outer body 12F and the dorsal side outer body 12B are formed without a misalignment in the sheet material 12S and are unlikely to be turned up, thereby providing favorable texture.

<One Example of an Underpants-Type Disposable Diaper>

Next, a specific example of an underpants-type disposable diaper will be described.

FIGS. 5 to 10 illustrate one example of an underpants-type disposable diaper. In this underpants-type disposable diaper, both side edges of a ventral side outer body 12F in a width direction and both side edges of a dorsal side outer body 12B in the width direction are joined along a vertical direction by heat sealing, ultrasonic welding, or the like to form cylindrical-shaped outer bodies 12F and 12B. In addition, on the outer bodies 12F and 12B, a front end portion of an inner body 200 is connected by a hot-melt adhesive or the like to an inner surface of a central portion of the ventral side outer body 12F in the width direction, and a back end portion of the inner body 200 is connected by the hot-melt adhesive or the like to the inner surface of a central portion of the dorsal side outer body 12B in the width direction. Reference sign 12A indicates a joined section (side seal portion) of the ventral side outer body 12F and the dorsal side outer body 12B. In addition, reference sign Y indicates the entire length (vertical length from an edge of a waist opening in the front panel F to an edge of the waist opening in the back panel B) of the diaper in the open state, and reference sign X indicates the entire width of the diaper in the open state.

The inner body 200 is a part absorbing and retaining excretion such as urine, and the outer bodies 12F and 12B are parts for supporting the inner body 200 for the wearer's body. The dot patterns in the drawing represent a hot-melt adhesive for joining the constituent members. Alternatively, the members may be joined by welding process (heat sealing or ultrasonic sealing). The hot-melt adhesive may be applied in a solid, bead, curtain, summit, or spiral pattern. Instead of or in addition to this, for fixation of the resilient and elastic members, the hot-melt adhesive may be applied to the outer peripheral surface of the resilient and elastic members by the means of a comb gun or a Sure-Wrap application means.

The upper opening of the outer bodies 12F and 12B constitutes a waist opening through which the wearer's waist is passed. Parts surrounded, respectively, by lower edges of the outer bodies 12F and 12B and side edges of the inner body 200 at both sides of the inner body 200 in the width direction constitute leg openings through which the wearer's legs are passed. With respective welded portions 12A taken off and the outer bodies 12F and 12B opened, the inner body 200 has a narrower shaped intermediate portion in the front-back direction, as illustrated in FIGS. 1 and 2. The inner body 200 extends from the dorsal side to the ventral side, passing through and covering the crotch portion. The inner body 200 is a portion receiving and absorbing excretion and retaining the liquid thereof, and the outer bodies 12F and 12B are portions to support the inner body 200 to the wearer.

(Inner Body)

Figure 7:
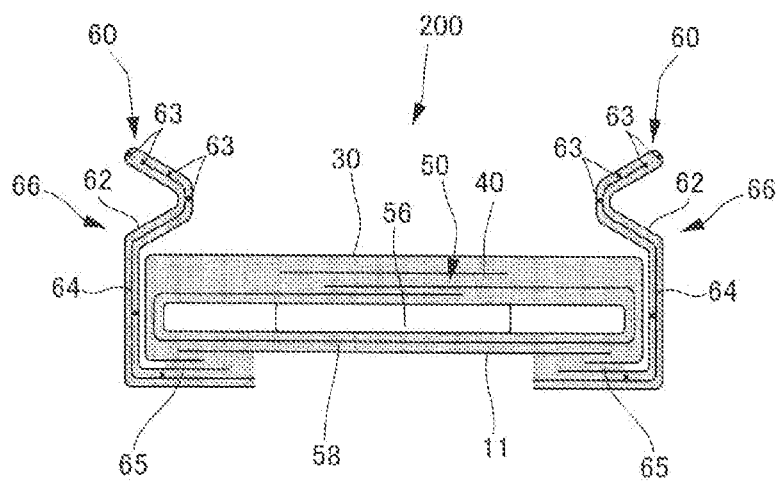
FIG. 7 is a cross-sectional view of FIG. 1 taken along line 3-3.
Figure 8:
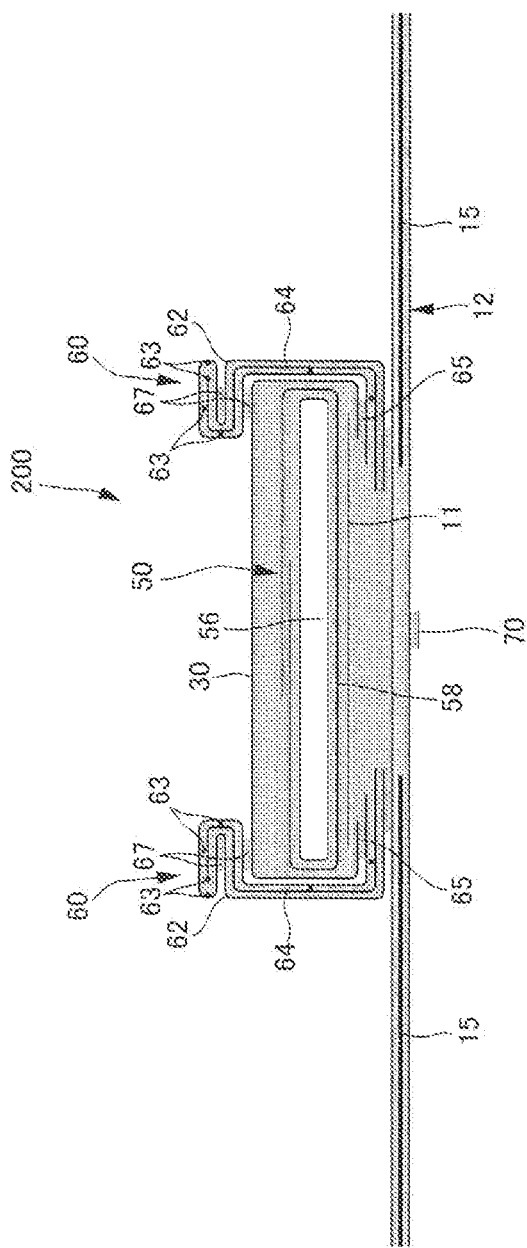
FIG. 8 is a cross-sectional view of FIG. 1 taken along line 4-4.
Figure 9:
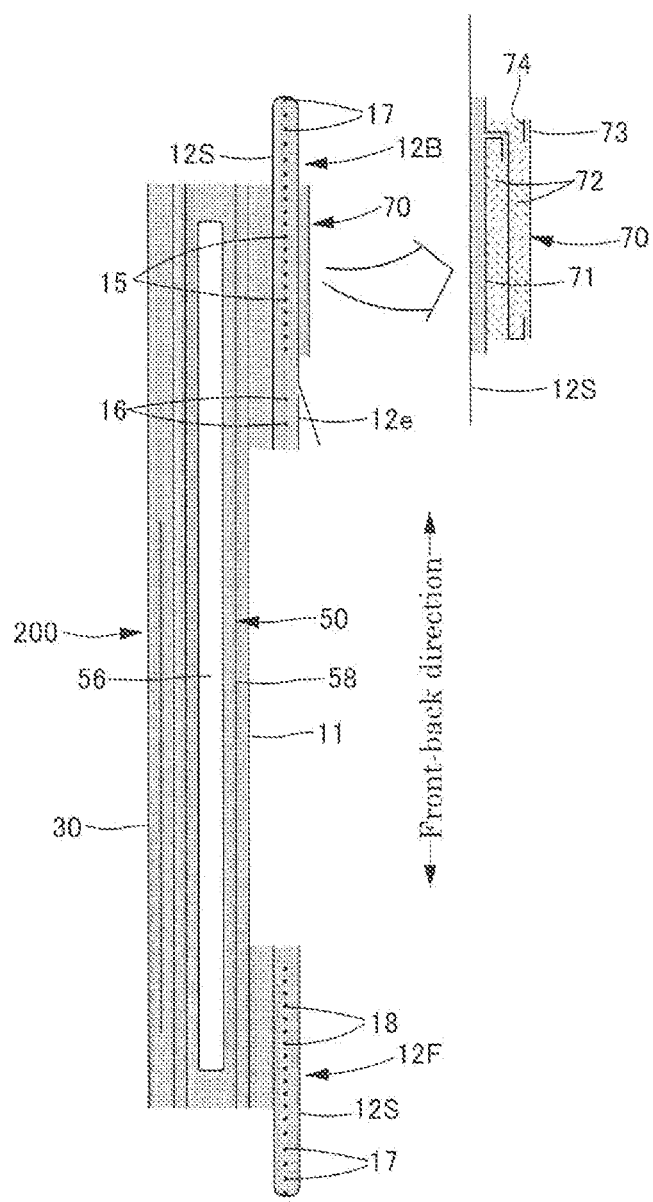
FIG. 9 is a cross-sectional view of FIG. 1 taken along line 5-5.

The inner body 200 may be formed in any shape, although it is rectangular in the illustrated form. The inner body 200 is a main body part with absorptive function that includes a top sheet 30 on the wearer's body side, a liquid impervious sheet 11, and an absorbent element 50 intervening between these sheets, as illustrated in FIGS. 7 to 9. Reference sign 40 indicates an interlayer sheet (second sheet) provided between the top sheet 30 and the absorbent element 50 to move quickly the liquid having passed through the top sheet 30 to the absorbent element 50 and to prevent reflowing. Reference sign 60 indicates three-dimensional gathers 60 standing from the both sides of the inner body 200 toward the wearer's body to prevent excretion from leaking toward the both sides of the inner body 200.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

In the case of providing the three-dimensional gathers 60, it is preferred that both sides of the top sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.
(Interlayer Sheet)

To move the liquid having passed through the top sheet 30 quickly to the absorber, the interlayer sheet (also called as "second sheet") 40 higher in liquid permeation speed than the top sheet 30 may be provided. The interlayer sheet 40 can not only move the liquid quickly to the absorber with enhancement in absorption performance of the absorber but also prevent a "reflowing" phenomenon of the absorbed liquid from the absorber to keep the top sheet 30 in a dry state at any time. The interlayer sheet 40 may not be provided.

The interlayer sheet 40 may be made from the same material as that for the top sheet 30, or spun-laced, spun-bonded, SMS, or pulp non-woven fabric, or mixture sheet of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) with high rigidity. The basis weight of the fiber is preferably 20 to 80 $g/m^2$, more preferably 25 to 60 $g/m^2$. The fineness of raw fibers for the non-woven fabric is preferably 2.2 to 10 dtex. To increase the bulk of the non-woven fabric, all or some composite fibers of the raw fibers are preferably eccentric fibers with cores not centered, hollow fibers, or eccentric and hollow fibers.

The interlayer sheet 40 in the illustrated form is centered on an absorber 56 and is narrower than the absorber 56 in the width direction. Alternatively, the interlayer sheet 40 may be provided over the entire width of the absorber 56. The interlayer sheet 40 may be the same in length as the absorber 56, or may be shorter than the absorber 56, falling within the central area for receiving liquid.
(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric and the like is laid on a plastic film. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filler in an olefin resin such as polyethylene and polypropylene to form a sheet and then elongating the sheet in a uniaxial or biaxial direction. Besides, the liquid impervious sheet 11 may be a non-woven fabric of microdenier fibers, or may be a liquid-impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the top sheet 30 side. The appropriate width of the extended portion is about 5 to 20 mm at each of the right and left sides.

An excretion indicator changing in color by absorption of liquid may be provided at the inside of the liquid impervious sheet 11, in particular, on the side surface of the absorber 56.
(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base portion, and stands obliquely toward the outside in the width direction from the intermediate portion to the forward edge.

More specifically, each of the three-dimensional gathers 60 is formed such that a belt-like gather sheet 62 having the same length as the length of the inner body 200 in the front-back direction is folded back in two in the width direction, and a plurality of elongated resilient and elastic members 63 is fixed in the extended state along the longitudinal direction with spacing therebetween in the width direction between the sheets at a folded portion and its neighborhood. The base portions (ends opposite to the sheet folded portion in the width direction) of the three-dimensional gathers 60 positioned opposite to the forward edge portions constitute attachment portions 65 fixed to the under side surface of the inner body 200 at side edges. The portions of the three-dimensional gathers 60 other than the attachment portions 65 constitute protrusions 66 (folded portions) that protrude from the attachment portions 65. In addition, the protrusions 66 include the base portions toward the central side in the width direction and the edge portions that are folded back from the edges of the base portions toward the outside in the width direction. Although this form uses the three-dimensional gathers of surface-touching type, three-dimensional gathers (not illustrated) of a line-touching type that are not folded back toward the outside in the width direction may also be used. Then, while the both ends of the protrusions 66 in the front-back direction are front-back fixed portions 67 which are fixed to the side surfaces of the top sheet 30 in a lying down state with a hot-melt adhesive or a heat seal, the intermediate portions positioned therebetween are unfixed free portions to which the elongated resilient and elastic members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 $g/m^2$. The elongated resilient and elastic members 63 may be rubber threads or the like. In the case of using spandex rubber threads, the fineness of the threads is preferably 470 to 1240 dtex, more preferably 620 to 940 dtex. The extension ratio of the threads at the time of fixing is preferably 150 to 350%, more preferably 200 to 300%. In addition, a water-proof film 64 may intervene in the gather sheet folded in two as illustrated in the drawing.

The number of elongated resilient and elastic members 63 provided in the free portions of the three-dimensional gathers 60 is preferably two to six, more specifically three to five. The arrangement spacing 60d is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 7. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Figure 10:
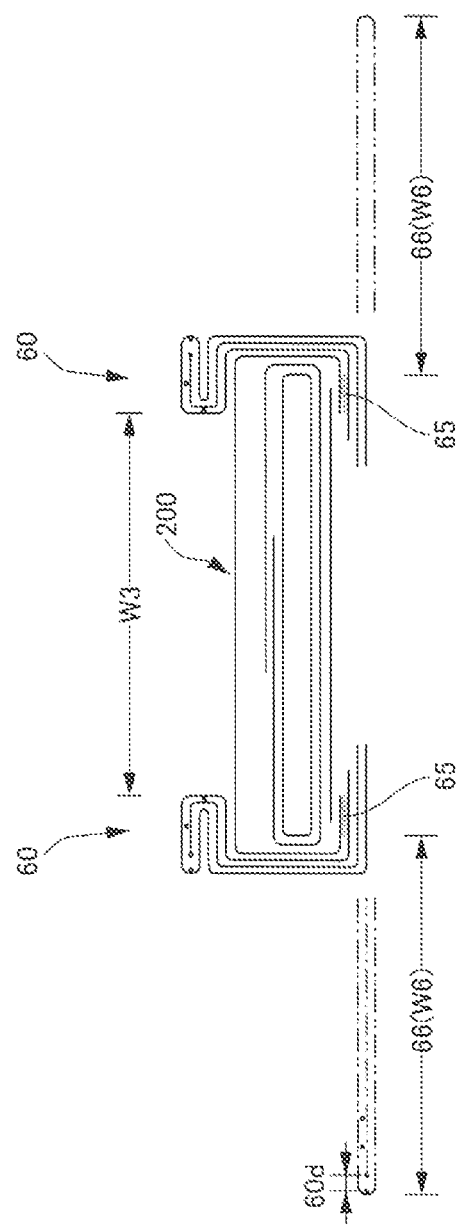
FIG. 10 is a cross-sectional view of only major components of the pants-type disposable diaper with dimensions.

The dimensions of the three-dimensional gathers 60 can be decided as appropriate. In the case of a disposable diaper for infants, however, the standing height W6 (width of the protrusions 66 in an open state) is preferably 15 to 60 mm, more specifically 20 to 40 mm as illustrated in FIG. 10, for example. In addition, the separation distance W3 between the folds at the innermost side is preferably 60 to 190 mm, more preferably 70 to 140 mm in the flatly folded state where the three-dimensional gathers 60 are made parallel to the surface of the top sheet 30.

Unlike the illustrated form, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

Figure 6:
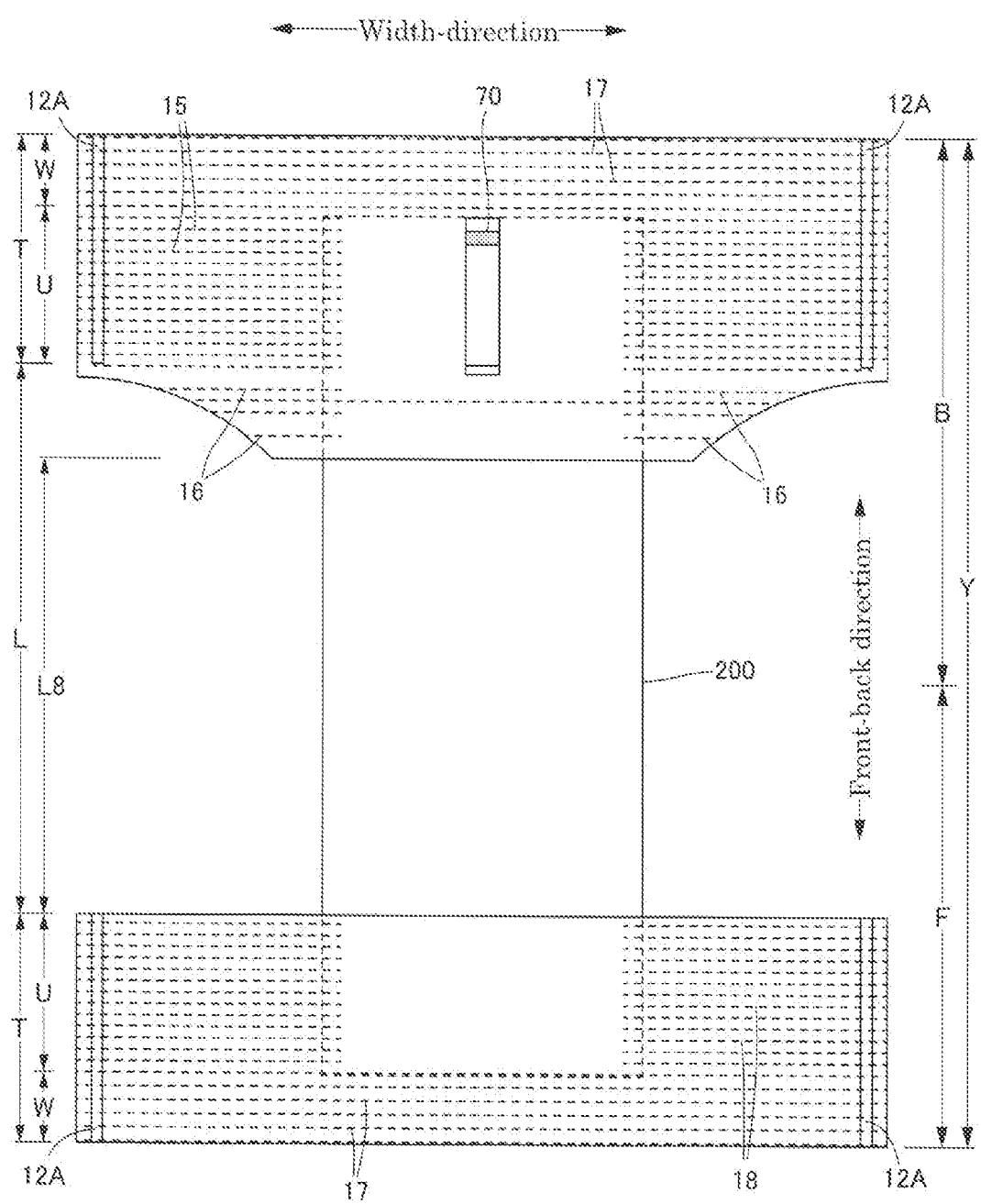
FIG. 6 is a plane view of outside of the pants-type disposable diaper in the open state.

The absorber 56 may be rectangular in shape but preferably has an hourglass shape having a front end portion, a back end portion, and a narrower portion that is positioned between the front and back end portions and is narrower than the two end portions as illustrated in FIG. 6 to improve the absorber 56 and the three-dimensional gathers 60 in a fit of the edges around the legs.

The dimensions of the absorber 56 can be decided as appropriate. Nevertheless, the absorber preferably extends to the peripheral edges or their neighborhoods of the inner body in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "powders" as well as "particles". The diameter of the high-absorbent polymer particles 54 may be the same as that of particles for general use in this type of absorbent article. For example, the ratio of particles that remain on a sieve after sieving (shaking for five minutes) with a standard sieve (JIS Z8801-1:2006) of 500 μm is preferably 30 weight % or less. Alternatively, the ratio of particles that remain on the sieve after sieving (shaking for five minutes) with the standard sieve (JIS Z8801-1:2006) of 180 μm is preferably 60 weight % or more.

There is no particular limitation on the material for the high-absorbent polymer particles but the material preferably has a water absorption capacity (JIS K7223-1996 "Testing method for water absorption capacity of super absorbent polymers") of 40 g/g or more. The high-absorbent polymer particles may be based on starch, cellulose, or synthetic polymer. The high-absorbent polymer particles may be made of a starch-acrylic acid (salt) graft copolymer, a saponified material of starch-acrylonitrile copolymer, a crosslinking substance of carboxymethyl-cellulose sodium, an acrylic acid (salt) polymer, or the like. The high-absorbent polymer particles are preferably used in a general particulate form but may be used in another form.

The water absorption rate (JIS K7224-1996 Testing method for water absorption rate of super absorbent polymers) of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The gel strength of the high-absorbent polymer particles is preferably 1000 Pa or more. Accordingly, it is possible to suppress effectively a sticky feeling of the absorber 56 after liquid absorption even when the absorber 56 is of high bulk.

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 $g/m^2$, in particular 10 to 30 $g/m^2$.

The form of wrapping by the wrapping sheet 58 can be decided as appropriate. Nevertheless, from the viewpoint of ease of producing and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the upper side surface and under side surface of the absorber 56 so that the extended portions are crushed in the upper side-under side direction and joined together by a joint means such as a hot-melt adhesive.

(Crotch Portion Cover Sheet)

To the back surface of the liquid impervious sheet in the inner body can be attached a crotch portion cover sheet so as to cover a part of exposed portion of the inner body (for example, along the entire front-back direction of the exposed portion between the ventral side outer body and the dorsal side outer body but not extending to the front and back ends of the inner body, or both side edges in the width direction not reaching the both side edges of the inner body) or the entire inner body. A material for the crotch portion cover sheet similar to that of the outer bodies and may be used as explained below.

(Outer Body)

The outer bodies 12F and 12B have waist portions T having the side seal portions 12A and determined as vertical areas (vertical areas from the waist opening WO to the upper ends of the leg openings LO) and an intermediate portion L determined as a front-back area of a portion forming the leg openings LO (between a vertical region of the ventral-side outer body 12F having the side seal portions 12A and a vertical region of the back-side outer body 12B having the side seal portions 12A). The waist portions T are conceptually divided into "waist edge portions" W forming the edge of the waist opening and "lower waist portions" U as the portions under the waist edge portions W. The lengths of these portions in the vertical direction vary depending on the size of the product and can be decided as appropriate. As an example, the length of the waist edge portion W may be 15 to 40 mm, and the length of the lower waist portion U may be 65 to 120 mm. On the other hand, the intermediate portion L can be also omitted or the intermediate portions L can be provided on both of the ventral-side outer body and the back-side outer body. In the form illustrated in the drawings, however, the intermediate portion L is provided on only the back-side outer body 12B and covers buttocks. When the edges of the intermediate portion L at the leg sides are formed into curved shapes so as to be around the legs, the fit around the legs are excellent and it is therefore preferable.

The outer bodies 12F and 12B are constituted by the ventral-side outer body 12F and the back-side outer body 12B, and the ventral-side outer body 12F and the back-side outer body 12B are not continuous at the leg sides and are separated from each other. A separation distance L8 therebetween may be set to approximately 150 to 250 mm.

The ventral side outer body 12F and the dorsal side outer body 12B have an inner layer and an outer layer formed by folding the sheet material 12S on the waist side, and elongated resilient and elastic members 15 to 18 such as rubber threads provided at a predetermined extension ratio between the inner layer and the outer layer to enhance the fit around the waist as illustrated in FIG. 9.

There is no specific limitation on the sheet material 12S as far as it is sheet-like, but it is preferably formed from non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. When the non-woven fabric is used, it is preferable that the basis weight thereof is approximately 10 to 30 $g/m^2$.

The elongated resilient and elastic members 15 to 19 may be made from a synthetic rubber or a natural rubber. To stick the sheet materials 12S of the outer bodies 12F and 12B and fix the elongated resilient and elastic members 15 to 18 sandwiched between the sheet materials 12S, a hot-melt adhesive can be used by various application methods, or heat sealing or ultrasonic adhesion can be used.

When the elongated resilient and elastic members 15 to 18 are used, same resilient and elastic members can be uniformly provided. It is preferable, however, to make fineness, spacing, or the like different depending on a position of the outer bodies 12F and 12B. Thus, in the illustrated form, a plurality of waist edge resilient and elastic members 17 is fixed at the waist edge portion W in the extended state along the width direction at a predetermined extension ratio with spacing therebetween in the up-down direction in such a manner as to be entirely continuous in the width direction. One or more of the waist edge resilient and elastic members 17 in a region adjacent to the lower waist portion U may overlap the inner body 200 or may be provided at the both sides of the central portion overlapping the inner body 200 in the width direction except for the central portion. As the waist edge resilient and elastic members 17, about 3 to 22 rubber threads with a fineness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 150 to 400%, in particular about 220 to 320%, with spacing of 4 to 12 mm. All of the waist edge resilient and elastic members 17 may not be equal in thickness and extension ratio. For example, the resilient and elastic members may be different in fineness and extension ratio between the upper and lower sides of the waist edge portions W.

In the lower waist portions U, a plurality of lower waist portion resilient and elastic members 15 and 18 composed of elongated resilient and elastic members is fixed at upper side and both sides of a central portion overlapping the inner body 200 in the width direction in such a manner as to be entirely continuous in the width direction in the extended state along the width direction at a predetermined extension ratio with up-down direction space therebetween.

As the lower waist portion resilient and elastic members 15 and 18, about 5 to 30 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 200 to 350%, in particular about 240 to 300%, with spacing of 1 to 15 mm, in particular 3 to 8 mm.

In the intermediate portion L, a plurality of intermediate portion resilient and elastic members 16 composed of elongated resilient and elastic members is fixed at both sides of a central portion overlapping the inner body 200 in the width direction in such a manner as to be entirely continuous in the width direction in the extended state along the width direction at a predetermined extension ratio with up-down direction space therebetween.

As the intermediate resilient ad elastic members 16 and the oblique resilient and elastic members 19, about 2 to 10 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 150 to 300%, in particular about 180 to 260%, with spacing of 5 to 40 mm, in particular 5 to 20 mm.

When the lower waist portion resilient and elastic members and the intermediate portion resilient and elastic members 15, 18, 16 are provided at the both sides of the center portions overlapping the inner body 200 in the width direction except for the center portions as illustrated in the drawings, the inner body 200 does not contract more than necessary in the width direction, thus the diaper does not become rough with deterioration in appearance and does not decrease in absorbing performance. The foregoing form includes the form in which the resilient and elastic members reside only at the both sides in the width direction, and the form in which the resilient and elastic members reside crossing over the inner body 200 from one side to the other side in the width direction, but the resilient and elastic members are finely cut and exert no contraction force at the center portion overlapping the inner body 200 in the width direction (this substantially means that no resilient and elastic members are provided), and thus the stretching force of the resilient and elastic members acts only at the both sides in the width direction. As a matter of course, the arrangement forms of the lower waist portion resilient and elastic members and the intermediate portion resilient and elastic members 15, 18, 16 are not limited to the foregoing examples. Alternatively, some or all of the lower waist portion resilient and elastic members and the intermediate portion resilient and elastic members 15, 18, 16 may be provided crossing over the inner body 200 from the one side to the other side in the width direction so that the contraction force acts on the entire lower waist portions U in the width direction.

In addition, characteristically, on both the ventral side outer body 12F and the dorsal side outer body 12B, the inner layer and the outer layer formed by folding the sheet material 12S extend up to the edge portions on the crotch side, an edge sheet material 12*e* intervenes between the leg-side edge portions in the outer layer and the inner layer of the dorsal side outer body 12B, the edge sheet material 12*e* and the inner layer are joined together, and the edge sheet material 12*e* and the outer layer are not joined except at the side seal portions 12A. The structure having the edge sheet material 12*e* is also applicable to the ventral side outer body 12F. Accordingly, the edge portion on the crotch side of the outer layer protrudes and appears like frills, thereby making the paper diaper suitable for girls in particular. In addition, the leg-side edges of the ventral side outer body 12F and the dorsal side outer body 12B are formed without the misalignment in the sheet material 12S and are unlikely to be turned up, thereby providing favorable texture. In this example, the edge sheet material 12*e* intervenes between the leg-side edge portion of the outer layer and the inner layer. Meanwhile, it is also proposed that the edge sheet material 12*e* is provided on the outer surface of the leg-side edge portion of the outer layer (not illustrated). In this case, the edge sheet material is joined to the outer body only at the crotch-side edge and the side seal portions, and the leg-side edges are formed from at least the inner layer and the outer layer, whereby the space between the edge sheet material and the outer layer is formed as a pocket-like portion opened on the waist side. This pocket may be provided in either the ventral side outer body or the dorsal side outer body.

(Tape for Disposal)

A tape for disposal 70 (fixing means) can be provided on the outer surface of the back panel B (in the illustrated example, the dorsal side outer body 12B) at the width direction central part. The tape for disposal 70 is intended to fasten the rolled or folded diaper 100 such that the top sheet 30 is positioned inside and the front panel F is positioned inside. In general, as illustrated in FIG. 9, the tape for disposal 70 has a base end portion 71 fixed to the outer surface of the back panel B by an adhesive or the like, a portion of the tape for disposal 70 close to the tip side than to the base end portion 71 is folded in three (with a Z-shaped cross section) or two, and the folded and overlapped portion is fixed in removable condition (tentatively fixed) by a tentative adhesive 72. The tape for disposal 70 also has a tab 73 colored in an opaque color such as white at the tip portion. The portion of the tape for disposal 70 other than the tab 73 is transparent or translucent. A design described later is visible from the outer surface of the tape for disposal 70 through the transparent or translucent portion of the tape for disposal 70. Specific structure of the tape for disposal 70 may be determined as appropriate. In the illustrated form, while the tape for disposal 70 is entirely formed by connecting a plurality of transparent or translucent base materials in a longitudinal direction, a colored tape 74 is stuck to the tab 73.

To discard the diaper 100, the diaper 100 is rolled or folded such that the top sheet 30 is positioned inside and the front panel F is positioned inside, the folded and overlapped portion of the tape for disposal 70 is removed and extended to wrap around the rolled or folded diaper 100 from the back panel B through the waist opening WO to the outer surface of the opposite side, and then is fixed by the adhesive. In particular, the tape for disposal 70 is preferably a three-folded type so that the tape for disposal 70 can be folded in a compact size when being not used and can be extended in a rectangular shape when being used.

The fixing means such as the tape for disposal 70 may be provided on the front panel F or on both the back panel B and the front panel F.

(Others)

The above are the specific examples of pants-type disposable diaper in the fifth form with the aforementioned outer structure example. As a matter of course, any other form can be used by changing the structure of the outer bodies 12F and 12B.

<Descriptions of the Terms Used Herein>

Unless otherwise specified herein, the terms used herein have the meanings described below.

"front-back (vertical) direction" refers to the direction linking the ventral side (front side) and the dorsal side (back side), and the "width direction" refers to the direction (right-left direction) orthogonal to the front-back direction. The "up-down direction" refers to the direction that becomes orthogonal to the waist direction when the diaper is worn, that is, when the diaper is folded into two at the crotch portion such that the front panel and the back panel are overlapped at the both sides, in other words, the direction linking a waist opening and a crotch portion.

The "extension ratio" refers to a value with respect to 100% representing the natural length.

The "gel strength" is measured in such a manner as described below. That is, a high-absorbent polymer of 1.0 g is added to an artificial urine of 49.0 g (urea: 20 wt %, salt: 8 wt %, calcium chloride dihydrate: 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).

The "basis weight" is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$.

If there is no description on environmental conditions in testing or measurements, the testing or the measurements shall be conducted in a test room or within a device under a normal state (a place of test shall be at temperatures of 20±5° C. and relative humidity of 60% or less).

INDUSTRIAL APPLICABILITY

The present invention is usable for an underpants-type disposable diaper and a production method therefor.

REFERENCE SIGNS LIST

L Intermediate portion
T Waist portion
U Lower waist portion
W Waist edge portion
11 Liquid impervious sheet
12B Dorsal side outer body
12A Side seal portion
12F, 12B Outer body
12F Ventral side outer body
12S Sheet material
12b Dorsal side elastic belt
12c CD direction intermediate portion
12d Separation portion
12e Edge sheet material
12f Ventral side elastic belt
12w Overlapped portion
15 to 18 Resilient and elastic member
17 Waist-edge portion resilient and elastic member
30 Top sheet
50 Absorbent element
56 Absorber
58 Wrapping sheet
60 Three-dimensional gather
62 Gather sheet
200 Inner body
301 Resilient member attachment step
302 Resilient member cutting step
303 Center slit step
304 Leg opening cutting and splitting step
305 Inner body attachment step
306 Folding step
307 Side part joining step
308 Cutoff step

The invention claimed is:

1. A production method for an underpants-type disposable diaper including:
    an outer body that is formed by joining a ventral side outer body and a dorsal side outer body at both sides; and
    an inner body that has a front part joined to a width direction central area of the ventral side outer body and a back part joined to a width direction central area of the dorsal side outer body and passes through the crotch portion of a wearer, the ventral side outer body and the dorsal side outer body being separated without being continued at the crotch side, wherein
    the production method comprises:
    supplying a belt-like continuous sheet material in a direction of continuity;
    disposing resilient and elastic members for imparting elasticity to the ventral side outer body and the dorsal side outer body at a CD direction intermediate portion of the sheet material;
    folding CD direction one side and other side parts across the CD direction intermediate portion of the sheet material toward the side of the CD direction intermediate portion with the resilient and elastic members, sandwiching and fixing the resilient and elastic members between the folded parts and the CD direction intermediate portion, and joining together the folded parts and the CD direction intermediate portion to form a belt-like continuous elastic belt;
    cutting the elastic belt at a CD direction intermediate position to split the elastic belt into a dorsal side elastic belt and a ventral side elastic belt, and then increasing a CD direction space between the dorsal side elastic belt and the ventral side elastic belt;
    supplying the inner body at MD direction intervals, joining the front part of the inner body to the ventral side elastic belt and the back part of the inner body to the dorsal side elastic belt to form an inner assembly body;
    folding double the inner assembly body in the CD direction, joining the ventral side elastic belt and the dorsal side elastic belt at parts to be both sides of each individual diaper, and cutting off the ventral side elastic belt and the dorsal side elastic belt at boundaries of each individual diaper to produce each individual diaper;

at the time of formation of the elastic belt, the CD direction one side part and other side part of the sheet material being folded to form an overlapped portion between an end of the folded part on the CD direction one side part and an end of the folded part on the CD direction other side part; and wherein an outer edge of the overlapped portion is a free edge without being joined with an inner edge of the overlapped portion, at the time of cutting the elastic belt, the elastic belt being cut in an area not having the outer edge of the folded parts.

2. The production method for an underpants-type disposable diaper according to claim 1, wherein the resilient and elastic members and a fixing means therefor, and a joining means for the sheet material are not provided in a region corresponding to the overlapped portion in the sheet material, and the sheet material in the region is joined only by the joining between the ventral side elastic belt and the dorsal side elastic belt.

3. The production method for an underpants-type disposable diaper according to claim 1, wherein the folded parts are positioned inside the diaper.

4. The production method for an underpants-type disposable diaper according to claim 1, wherein the folded parts are positioned outside the diaper.

5. The production method for an underpants-type disposable diaper according to claim 1, wherein, after the formation of the elastic belt, some of the resilient and elastic members in a region to be the ventral side elastic belt and some of the resilient and elastic members in a region to be the dorsal side elastic belt are finely divided before the elastic belt is split into the ventral side elastic belt and the dorsal side elastic belt.

6. The production method for an underpants-type disposable diaper according to claim 1, wherein at least a CD direction central end portion of at least one of the dorsal side elastic belt and the ventral side elastic belt is formed as a region in which a plurality of layers in the sheet material is layered by forming the elastic belt and splitting the elastic belt into the dorsal side elastic belt and the ventral side elastic belt, and cutting is performed within the region to form edges of leg openings in a curved shape.

* * * * *